United States Patent [19]

Fukao et al.

[11] Patent Number: 5,347,062
[45] Date of Patent: Sep. 13, 1994

[54] PROCESS FOR PREPARING ALKYL-SUBSTITUTED AROMATIC HYDROCARBONS

[75] Inventors: Masami Fukao, Shiga; Takuo Hibi, Osaka; Kazuo Kimura, Osaka; Masahiro Usui, Chiba; Gohfu Suzukamo, Osaka, all of Japan

[73] Assignee: Sumitomo Chemical Co., Ltd., Osaka, Japan

[21] Appl. No.: 21,852

[22] Filed: Feb. 24, 1993

Related U.S. Application Data

[60] Division of Ser. No. 815,889, Jan. 7, 1992, Pat. No. 5,227,559, which is a continuation of Ser. No. 570,548, Aug. 21, 1990, abandoned, which is a continuation-in-part of Ser. No. 305,755, Feb. 3, 1989, abandoned.

[30] Foreign Application Priority Data

| Feb. 3, 1988 | [JP] | Japan | 63-24527 |
| Aug. 10, 1988 | [JP] | Japan | 63-200794 |
| Nov. 8, 1988 | [JP] | Japan | 63-282933 |
| Dec. 27, 1988 | [JP] | Japan | 63-331081 |

[51] Int. Cl.$^5$ ............................................. C07C 2/66
[52] U.S. Cl. .................................. 585/452; 585/453; 585/455; 585/467
[58] Field of Search ............... 585/467, 452, 446, 453, 585/455

[56] References Cited

U.S. PATENT DOCUMENTS

| 3,808,152 | 5/1974 | Nagase et al. | 252/463 |
| 4,388,480 | 6/1983 | Imai et al. | 585/516 |
| 4,511,748 | 4/1985 | Kudoh et al. | 585/467 |
| 4,620,056 | 10/1986 | Shimizu et al. | 585/452 |
| 4,711,873 | 12/1987 | Suzukamo et al. | 502/344 |

FOREIGN PATENT DOCUMENTS

| 676554 | 12/1963 | Canada. |
| 0128001 | 12/1984 | European Pat. Off. |
| 0173335 | 3/1986 | European Pat. Off. |
| 0211448 | 8/1986 | European Pat. Off. |
| 6153229 | 8/1984 | Japan. |
| 857894 | 1/1961 | United Kingdom. |
| 1259535 | 8/1969 | United Kingdom. |
| 1269280 | 4/1972 | United Kingdom. |

OTHER PUBLICATIONS

"Base–Catalyzed Reactions of Hydrocarbons and Related Compounds," H. Pines, W. Stalic, Academic Press, pp. 240–309, 1977.

"Carbanions Additions in the Reaction of Aromatic Hydrocarbons with Monoolefins," H. Pines, V. Mark, Recvd. Mar. 14, 1956, pp. 4316–4322.

"Nippon Petrochem KK Abstract" J6 1053–229–A, p. 23, 1984.

*Primary Examiner*—Asok Pal
*Assistant Examiner*—P. Achutamurthy

[57] ABSTRACT

An alkyl-substituted hydrocarbon is prepared by alkylating an aromatic hydrocarbon having at least one hydrogen atom at an alpha-position in a side chain with an olefin in the presence of a solid base which is obtainable by heating an alumina, an alkali metal hydroxide and an alkali metal or an alumina containing at least 1.3% by weight of water and an alkali metal in an inert gas atmosphere at a specific temperature as a catalyst.

15 Claims, No Drawings

PROCESS FOR PREPARING ALKYL-SUBSTITUTED AROMATIC HYDROCARBONS

CROSS REFERENCE TO RELATED APPLICATIONS

This application is a divisional of copending application Ser. No. 07/815,889, filed on Jan. 7, 1992, U.S. Pat. No. 5,227,559 which is a Rule 62 continuation of application Ser. No. 07/570,548, filed on Aug. 21, 1990, now abandoned, which is a continuation-in-part of application Ser. No. 07/305,755, filed on Feb. 3, 1989, now abandoned, the entire contents all these application hereby being incorporated by reference.

BACKGROUND OF THE INVENTION

Field of the Invention

The present invention relates to a process for preparing an alkyl-substituted aromatic hydrocarbon. More particularly, the present invention relates to a process for preparing an alkyl-substituted aromatic hydrocarbon by reacting an alkyl-substituted aromatic hydrocarbon having at least one hydrogen atom at an alpha-position in said alkyl side chain with an olefin in the presence of a solid base which is prepared from an alumina, an alkali metal hydroxide and an alkali metal or from water-containing alumina and an alkali metal at a temperature in a specific range, whereby the alpha position is alkylated.

The alkyl-substituted aromatic hydrocarbons are useful as intermediates in the production of fine chemicals such as agricultural chemicals, medicines and other chemicals and prepared by reacting the aromatic hydrocarbon having the hydrogen atom at the alpha-position in the side chain with the olefin in the presence of a base catalyst.

As the preparation process of the alkyl-substituted aromatic hydrocarbon, there is known a process which utilizes a catalyst comprising metal sodium and chlorotoluene and a process which utilizes a catalyst comprising metal sodium supported on potassium carbonate (cf. J. Am. Chem. Soc., 78, 4316 (1956), GB Patent No. 1269280 and Japanese Patent Kokai Publication No. 53229/1986).

However, the conventionally used catalysts have various drawbacks such as insufficient catalytic activities, a low yield of the alkyl-substituted hydrocarbon per a unit amount of the catalyst and troublesome separation of the catalysts from the product. Further, the conventional catalysts suffer from such problem that when they contact the oxygen and/or moisture in the air, they tend to lose their activities or they are ignited.

SUMMARY OF THE INVENTION

One object of the present invention is to provide a base catalyst which effectively catalyzes the reaction of the aromatic hydrocarbon having the hydrogen atom at the alpha-position in the side chain with the olefin, can be easily separated from the product after reaction.

Another object of the present invention is to provide a process for producing an alkyl-substituted hydrocarbon by reacting the aromatic hydrocarbon having the hydrogen atom at the alpha-position in the side chain with the olefin.

Accordingly, the present invention provides a process for preparing an alkyl-substituted hydrocarbon comprising alkylating an aromatic hydrocarbon having a hydrogen atom at an alpha-position in a side chain with an olefin in the presence of a solid base which is obtainable by heating an alumina, an alkali metal hydroxide and an alkali metal or an alumina containing at least 1.3% by weight of water and an alkali metal in an inert gas atmosphere at a temperature of 200° to 600° C. as a catalyst.

DETAILED DESCRIPTION OF THE INVENTION

The process of the present invention is characterized in the use of the specific solid base as the catalyst, which solid base is prepared by heating the alumina, the alkali metal hydroxide and the alkali metal at the specific temperature.

As the alumina, various types of aluminas except α-alumina are used. Preferred examples of the alumina are γ-alumina, χ-alumina and ρ-alumina. Among them, those having a relatively large surface area are preferred.

As the alkali metal, an alkali metal of Group I of the Periodic Table such as lithium, sodium, potassium and rubidium is used. They may be used as a mixture or an alloy. Among them, sodium, potassium and an alloy of them, particularly potassium are preferred. The amount of the alkali metal is generally from 2 to 15% by weight based on the weight of the alumina.

As the alkali metal hydroxide, any of hydroxides of the above exemplified alkali metals may be used. Preferably, sodium hydroxide, potassium hydroxide and cecium hydroxide are used. Mixtures of two or more alkali metal hydroxides may be used. The amount of the alkali metal hydroxide is generally from 5 to 40% by weight based on the weight of the alumina.

In the preparation of the solid base, preferably the alumina is treated with the alkali metal hydroxide, and then the resulting product is reacted with the alkali metal in the inert gas atmosphere.

For example, the alumina is heated to a desired temperature and mixed with the alkali metal hydroxide while stirring. Thereafter, the alkali metal is added to the resulting product and heating of the resulting mixture is continued while stirring. Alternatively, the alkali metal hydroxide can be used in the form of an aqueous solution, provided that water in such solution is sufficiently removed prior to the addition of the alkali metal. Thereafter, the alkali metal is added to the dried product and further heated.

As the inert gas, nitrogen, helium, argon and the like are used.

In the preparation of the solid base to be used in the process of the present invention, the reaction temperature is important. Usually, the reaction temperature is from 200° to 600° C. Preferably, the alumina and the alkali metal hydroxide are reacted in a temperature range of 250° to 550° C., more preferably in a temperature range of 260° to 480° C., and the alkali metal is reacted in a temperature range of 200° to 450° C.

Moreover, in the case of the solid base which is prepared by using sodium as an alkali metal and potassium hydroxide as an alkali metal hydroxide, the alumina and potassium hydroxide are reacted in a temperature range of 200° to 390° C., more preferably in a temperature range of 270° to 390° C.

The reaction time varies with other reaction conditions such as the reaction temperature. The reaction of the alumina with the alkali metal hydroxide may be completed within 0.5 to 10 hours, and the treatment with the alkali metal may be completed within 10 to 300 minutes.

By the above reactions, the solid base which has high catalytic activity, good flowability and handleability can be obtained.

When water-containing alumina containing at least 1.3% by weight of water is used as the alumina, the solid base having the same catalytic performances as above can be prepared with using no alkali metal hydroxide. Namely, the solid base catalyst can be prepared by reacting the alumina containing at least 1.3% by weight of water with the alkali metal in the inert gas atmosphere at a temperature of 200° to 600° C.

Various types of water-containing aluminas except for α-alumina can be used.

Generally, alumina is produced by calcining aluminum hydroxide. According to the calcining temperature and time, alumina has various metastable states and a water content varies so that various type of alumina are produced. In the present invention, such alumina may be used. Preferably, water-containing alumina with a large surface area such as γ-alumina, χ-alumina, ρ-alumina and η-alumina are used.

The water content may be expressed by weight loss on heating in the heating step in which the alumina in its original state is converted to α-alumina which is considered to include no removable water. Usually, the water content of the water-containing alumina is 1.3 to 15% by weight, preferably 2 to 10% by weight.

The amount of alkali metal used in this preparation method is generally from 1.01 to 2 time molar equivalents of water contained in the alumina.

Again, the reaction temperature is important in this preparation method of the catalyst. Usually, the reaction temperature is from 200° to 600° C., preferably from 250° to 550° C., more preferably from 260° to 480° C.

The reaction time varies with other reactions-conditions such as the reaction temperature. The reaction of the alumina and the alkali metal may be completed within 10 to 300 minutes.

By the above reaction, the solid base which has the same properties as that prepared from the alumina, the alkali metal hydroxide and the alkali metal, such as high catalytic activity, good flowability and handleability can be obtained. This may be because a part of the alkali metal reacts with the water contained in the alumina to form the corresponding alkali metal hydroxide and as the result, the alumina, the alkali metal hydroxide and the alkali metal react with each other.

In the process of the present invention, the aromatic hydrocarbon having the hydrogen atom at the alpha-position in the side chain is reacted with the olefin in the presence of the above described solid base as the catalyst.

As such aromatic hydrocarbon, not only monocyclic aromatic hydrocarbons but also condensed polycyclic aromatic hydrocarbons may be used. In the aromatic hydrocarbons, the side chains may be closed to form a ring. Specific examples of the aromatic hydrocarbon are toluene, ethylbenzene, isopropyl-benzene (cumene), n-propylbenzene, n-butylbenzene, sec.-butylbenzene, isobutylbenzene, xylene, cymene, diisopropylbenzene, methylnaphthalene, tetrahydronaphthalene, indan and the like. Among them, toluene, ethylbenzene and isopropylbenzene are preferred.

As the olefin, those having 2 to 20 carbon atoms are usually used. The olefin may be straight or branched. The carbon-carbon double bond may be a terminal or internal double bond. Preferably, the olefin having the terminal double bond is used. Specific examples of the olefin are ethylene, propylene, 1-butene, 2-butene, isobutylene, 1-pentene, 2-pentene, 1-hexene, 2-hexene, 3-hexene, 1-heptene, 2-heptene, 3-heptene, octene, nonene, 3-methyl-1-butene, 2-methyl-2-butene, 3-methyl-1-pentene, 3-methyl-2-pentene and the like. Among them, ethylene, propylene, 1-butene and 2-butene are preferred.

The alkylation reaction according to the present invention may be carried out batchwise or continuously with the use of a fluidized bed or a fix bed.

The reaction temperature for the alkylation is usually from 0° to 300° C., preferably from 20° to 200° C.

The reaction pressure is from atmospheric pressure to 200 kg/cm$^2$, preferably from 2 to 100 kg/cm$^2$.

The molar ratio of the olefin to the aromatic hydrocarbon is usually from 0.1 to 10, preferably from 0.2 to 5.

In the batchwise reaction, the amount of solid base catalyst to be used is from 0.1 to 20% by weight, preferably from 0.2 to 5% by weight based on the weight of the aromatic hydrocarbon. The reaction time is generally from 0.5 to 50 hours, preferably from 1 to 25 hours.

In the continuous reaction, the mixture of the aromatic hydrocarbon and the olefin in the above molar ratio is supplied at LHSV of 0.1 to 600 hr$^{-1}$, preferably 0.5 to 400 hr$^{-1}$.

According to the present invention, the alkyl-substituted hydrocarbon is effectively prepared in the presence of the solid base catalyst in a small amount under the mild conditions. Further, the catalyst to be used according to the present invention is easily handled and post-treated after the reaction.

PREFERRED EMBODIMENTS OF THE INVENTION

Practically and presently preferred embodiments of the present invention will be illustrated by following examples.

Preparation of Solid Bases

Solid Base A

42–200 Mesh activated alumina (NKHD-24, a trade name of Sumitomo Chemical Co., Ltd.) (26.5 g) was stirred in an atmosphere of nitrogen at 500° C. for 2 hours and cooled to 350° C. Then, potassium hydroxide (2.5 g) was added to the alumina and the mixture was stirred at 350° C. for 3 hours followed by cooling to 290° C.

To the mixture, metal potassium (2.0 g) was added and the mixture was stirred at 290° C. for 0.5 hour followed by cooling to room temperature to obtain Solid Base A (24 g).

Solid Base B

In the same manner as in the preparation of Solid Base A but adding potassium hydroxide at 250° C. and stirring the mixture of the alumina and potassium hydroxide at 250° C., Solid Base B was prepared.

Solid Base C

In the same manner as in the preparation of Solid Base A but adding potassium hydroxide at 480° C. and stirring the mixture of the alumina and potassium hydroxide at 480° C., Solid Base C was prepared.

Solid Base D

In the same manner as in the preparation of Solid Base A but stirring the activated alumina at 580° C. for 1 hour, adding potassium hydroxide at 580° C. and stirring the mixture of the alumina and potassium hydroxide at 580° C., Solid Base D (24.1 g) was prepared.

Solid Base E

In the same manner as in the preparation of Solid Base A but using sodium hydroxide (2.5 g) in place of potassium hydroxide, Solid Base E (24.1 g) was prepared.

Solid Base F

In the same manner as in the preparation of Solid Base A but using sodium hydroxide (2.5 g) in place of potassium hydroxide and using metal sodium (2.0 g) in place of metal potassium, Solid Base F was prepared.

Solid Base G

Activated alumina having the average central particle size of 80 μm (BK-570, a trade name of Sumitomo Chemical Co., Ltd.) (50 g) was stirred in an atmosphere of nitrogen at 500° C. for 1 hour and cooled to 350° C. Then, potassium hydroxide (5.65 g) was added to the alumina and the mixture was stirred at 350° C. for 3 hours followed by cooling to 290° C. To the cooled mixture, metal potassium (4.06 g) was added and the resulting mixture was stirred at 290° C. for 0.2 hour followed by cooling to room temperature to obtain Solid Base G (55.2 g).

Solid Base H

In the same manner as in the preparation of Solid Base G but using 4.02 g of metal potassium, adding metal potassium at 350° C. and stirring the resulting mixture at 350° C., Solid Base H was prepared.

Solid Base I

In the same manner as in the preparation of Solid Base G but using 4.15 g of metal potassium, adding metal potassium at 220° C. and stirring the resulting mixture at 220° C., Solid Base I was prepared.

Solid Base J

In the same manner as in the preparation of Solid Base G but using 50 g of 48-200 mesh activated alumina (NKH 3-24), 4.73 g of potassium hydroxide and 2.29 g of metal potassium, Solid Base J was prepared.

Solid Base K

The same activated alumina as used in the preparation of Solid Base A (26.5 g) and potassium hydroxide (2.5 g) were ground and mixed and then placed in a crucible and heated at 1,200° C. for 3 hours in a muffle furnace. The mixture was cooled to 200° C. and further to room temperature in a desiccator in an atmosphere of nitrogen to obtain a fine powder.

The fine powder was heated to 290° C. Then, to the heated powder, metal potassium (2.0 g) was added while stirring. The mixture was further stirred at 290° C. for 0.5 hour followed by cooling to room temperature to obtain Solid Base K.

Solid Base L

In the same manner as in the preparation of Solid Base K but using 2.0 g of metal sodium in place of metal potassium, Solid Base L was prepared.

Solid Base M

In the same manner as in the preparation of Solid Base K but heating the mixture of the activated alumina and potassium hydroxide at 900° C. in the muffle furnace, Solid Base M was prepared.

EXAMPLE 1

In a 600 ml autoclave equipped with a magnetic stirrer, Solid Base A (0.39 g) and cumene (240 g) were charged under nitrogen, heated to 105° C. while stirring and then reacted at the same temperature for 1.5 hours while supplying ethylene gas under pressure of 10 kg/cm²G. to produce tert.-amylbenzene (hereinafter referred to as "TAB").

After the reaction, the autoclave was cooled, and the catalyst was filtered off. The reaction mixture was analyzed with gas chromatography. The results are shown in Table 1.

The selectivity of TAB is calculated according to the following equation:

$$\text{Selectivity (\%)} = \frac{\text{Amount of produced } TAB \text{ (mole)} \times 100}{\text{Total amount of all produced alkyl-substituted compounds (mole)}}$$

TABLE 1

| Example No. | Solid Base (g) | Reaction Temp. (°C.) | Reaction Time (hrs) | Conversion of cumene (%) | Selectivity of TAB (%) |
|---|---|---|---|---|---|
| 1 | 0.39 | 105 | 1.5 | 85.5 | 99.4 |
| 2 | 0.37 | 160 | 3 | 99.8 | 99.3 |
| 3 | 0.38 | 42 | 1.5 | 46.9 | 99.6 |

EXAMPLES 2-3

In the same manner as in Example 1 but carrying out the reaction under the conditions shown in Table 1, the alkylation was carried out. The results are shown in Table 1.

EXAMPLES 4-9 AND COMPARATIVE EXAMPLES 1-2

In the same manner as in Example 1 but using one of Solid Bases A to F, K and L and 160 g of cumene and carrying out the reaction at 160° C., the alkylation was carried out. The results are shown in Table 2.

In Examples 1-9, the catalyst was still active at the end of the reaction and the alkylation could be further carried out by using the same catalyst.

TABLE 2

| Example No. | Solid Base Kind | Solid Base grams | Conversion of Cumene (%) | Selectivity of TAB (%) |
|---|---|---|---|---|
| 4 | A | 0.44 | 94.9 | 99.5 |
| 5 | B | 0.74 | 87.6 | 99.3 |
| 6 | C | 0.43 | 92.9 | 97.9 |
| 7 | D | 0.45 | 40.4 | 88.9 |
| 8 | E | 0.43 | 76.3 | 98.9 |
| 9 | F | 0.90 | 61.1 | 99.7 |
| Comp. 1 | K | 0.88 | 20.2 | 70.7 |
| Comp. 2 | L | 0.98 | 7.5 | 98.4 |

EXAMPLE 10

In a 230 ml autoclave equipped with a magnetic stirrer, Solid Base G (0.85 g) and cumene (88 g) were charged under nitrogen, heated to 162° C. while stirring and then reacted at the same temperature for 6.5 hours while supplying ethylene gas under pressure of 30 kg/cm$^2$G to produce TAB. After the reaction, the product was analyzed in the same manner as in Example 1 to find that the conversion of cumene was 88% and the selectivity of TAB was 100%.

EXAMPLE 11

In a 300 ml autoclave equipped with a magnetic stirrer, Solid Base A (0.86 g) and cumene (80 g) were harged under nitrogen and then liquid propylene (120 ml) was injected under pressure. The reaction was then carried out at 160° C. for 36 hours while stirring to produce 1,1,2-trimethylpropylbenzene (hereinafter referred to as "TMPB").

After the reaction, the autoclave was cooled, and the reaction mixture was analyzed in the same manner as in Example 1. The results are shown in Table 3.

The selectivity of TMPB is calculated according to the following equation:

$$\text{Selectivity (\%)} = \frac{\text{Amount of produced } TMPB \text{ (mole)} \times 100}{\text{Total amount of all produced alkyl-substituted compounds (mole)}}$$

EXAMPLES 12-15

In the same manner as in Example 11 but using one of Solid Bases G to J in place of Solid Base A and an 230 ml autoclave in Example 12 and carrying out the reaction under the conditions shown in Table 3, the alkylation was carried out. The results are shown in Table 3.

In Examples 11-15, the catalyst was still active at the end of the reaction and the alkylation could be further carried out by using the same catalyst.

TABLE 3

| Example No. | Solid Base Kind | grams | Cumene (g) | Propylene (ml) | Temp. (°C.) | Time (hrs) | Conversion of cumene (%) | Selectivity of TMPB (%) |
| --- | --- | --- | --- | --- | --- | --- | --- | --- |
| 11 | A | 0.86 | 80 | 120 | 160 | 36 | 77.8 | 86.0 |
| 12 | G | 1.92 | 88 | 94 | 162 | 21 | 69.0 | 87.2 |
| 13 | H | 1.62 | 79.5 | 90 | 160 | 24 | 78.1 | 88.0 |
| 14 | I | 1.66 | 79 | 85 | 160 | 24 | 56.2 | 89.5 |
| 15 | J | 1.19 | 80 | 80 | 160 | 24 | 48.4 | 88.0 |

COMPARATIVE EXAMPLE 3

In a 200 ml autoclave equipped with a magnetic stirrer, anhydrous potassium carbonate which had been calcined at 400° C. for 2 hours in a nitrogen atmosphere (8.86 g), metal sodium 0.30 g) and cumene (81.2 g) were charged under nitrogen, heated to 190° C. and then stirred at the same temperature for 2 hours.

After cooling the autoclave, liquid propylene (70 ml) was injected under pressure and the mixture was stirred at 160° C. for 24 hours.

After the reaction, the product was analyzed in the same manner as in Example 1 to find that the conversion of cumene was 8.0% and the selectivity of TMPB was 81.5%.

EXAMPLE 16

In a 300 ml autoclave equipped with a magnetic stirrer, Solid Base A (4.07 g) and toluene (79.5 g) were charged under nitrogen and then liquid propylene (70 ml) was injected under pressure. The mixture was stirred at 163° C. for 6 hours to obtain isobutylbenzene (hereinafter referred to as "IBB").

After the reaction, the product was analyzed in the same manner as in Example 1. The results are shown in Table 4. The selectivity of IBB is calculated according to the following equation:

$$\text{Selectivity (\%)} = \frac{\text{Amount of produced } IBB \text{ (mole)} \times 100}{\text{Total amount of all produced alkyl-substituted compounds (mole)}}$$

EXAMPLES 17-20 AND COMPARATIVE EXAMPLE 4

In the same manner as in Example 16 but using one of Solid Bases B to D, J and M in place of Solid Base A, the reaction was carried out. The results are shown in Table 4.

In Examples 16-20, the catalyst was still active at the end of the reaction and the alkylation could be further carried out by using the same catalyst.

TABLE 4

| Example No. | Solid Base Kind | grams | Conversion of Toluene (%) | Selectivity of IBB (%) |
| --- | --- | --- | --- | --- |
| 16 | A | 4.07 | 36.3 | 91.8 |
| 17 | B | 4.19 | 26.6 | 90.7 |
| 18 | C | 3.45 | 28.2 | 91.5 |
| 19 | D | 3.29 | 17.8 | 93.6 |
| 20 | J | 3.61 | 29.8 | 92.0 |
| Comp. 4 | M | 3.37 | 8.6 | 85.0 |

COMPARATIVE EXAMPLE 5

In a 200 ml autoclave equipped with a magnetic stirrer having a nitrogen interior atmosphere, anhydrous potassium carbonate which had been calcined at 400° C. for 2 hours in a nitrogen atmosphere (8.45 g), metal sodium 0.30 g) and toluene (26.6 g) were charged and then stirred at 190° C. for 2 hours.

After cooling the autoclave, additional toluene (53.2 g) was added and liquid propylene (70 ml) was injected under pressure. Then the mixture was stirred at 160° C. for 6 hours.

After the reaction, the product was analyzed in the same manner as in Example 1 to find that the conversion of toluene was 3.5% and the selectivity of IBB was 88.2%.

EXAMPLE 21

In a 200 ml autoclave equipped with a magnetic stirrer, Solid Base J (0.7 g) and toluene (81 g) were charged under nitrogen, heated to 160° C. and then reacted at the same temperature for 6 hours while supplying ethylene gas under pressure of 10 kg/cm$^2$G.

After the reaction, the product was analyzed in the same manner as in Example 1 to find that the conversion of toluene was 28.2%, the selectivity of n-pryopylbenzene was 78.6% and the selectivity of 1-ethylpropylbenzene was 20.9%.

Preparation of Solid Bases

Solid Base N

To 40-200 mesh activated alumina containing 3.6% of water (21.7 g) heated at 290° C. in an atmosphere of nitrogen, metal potassium (2.08 g) was added while stirring and the mixture was further stirred at the same temperature for 0.2 hour followed by cooling to room temperature to obtain Solid Base N (23.2 g).

Solid Base O

In the same manner as in the preparation of Solid Base N but using 2.5 g of metal potassium, changing the temperature to 350° C. and heating the mixture of the alumina and metal potassium for 0.4 hour while stirring, Solid Base O was prepared.

Solid Base P

In the same manner as in the preparation of Solid Base N but changing the temperature to 150° C., Solid Base P was prepared.

Solid Base Q

To 40-200 mesh activated alumina containing 1.0% of water (21.8 g) heated at 290° C. in an atmosphere of nitrogen, metal potassium (2.0 g) was added while stirring and the mixture was further stirred at the same temperature for 0.2 hour followed by cooling to room temperature to obtain Solid Base Q.

Solid Base R

To the same water-containing alumina as used in the preparation of Solid Base N (21.7 g) heated at 290° C. in an atmosphere of nitrogen, metal potassium (0.88 g) was added while stirring and the mixture was further stirred at the same temperature for 1 hour.

Then, the mixture was poured in a crucible and heated at 1,200° C. for 3 hours in a muffle furnace. The mixture was cooled to 200° C. and further to room temperature in a desiccator in an atmosphere of nitrogen.

After heating the mixture to 290° C. in an atmosphere of nitrogen, metal potassium (1.2 g) was added and the mixture was stirred at 290° C. for 0.2 hour followed by cooling to room temperature to obtain Solid Base R.

Solid Base S

To activated alumina containing 1.1% by weight of water and having the average central particle size of 80 μm (18.9 g), metal potassium (1.59 g) was added at 290° C. while stirring in an atmosphere of nitrogen and the mixture was further stirred at the same temperature for 0.2 hour followed by cooling to room temperature to obtain Solid Base S.

Example 22

In a 600 ml autoclave equipped with a magnetic stirrer, Solid Base N (0.45 g) and cumene (240 g) were charged under nitrogen, heated to 160° C. while stirring at 1,000 rpm and then reacted at the same temperature for 2 hours while supplying ethylene gas under pressure of 10 kg/cm$^2$G. to produce TAB.

After the reaction, the autoclave was cooled, and the product was analyzed with gas chromatography. The results are shown in Table 5.

EXAMPLE 23 AND COMPARATIVE EXAMPLES 6-7

In the same manner as in Example 22 but using one of Solid Bases O, Q and R in place of Solid Base N, the alkylation was carried out. The results are shown in Table 5.

In Examples 22 and 23, the catalyst was still active at the end of the reaction and the alkylation could be further carried out by using the same catalyst.

COMPARATIVE EXAMPLE 8

In a 200 ml autoclave equipped with a magnetic stirrer, anhydrous potassium carbonate which had been calcined at 400° C. for 2 hours in a nitrogen atmosphere (8.19 g), metal sodium (0.30 g) and cumene (26.7 g) were charged under nitrogen, heated to 190° C. and then stirred at 1,000 rpm at the same temperature for 2 hours.

After cooling the autoclave, cumene (53.3 g) was further added, and the mixture was heated to 160° C. while stirring at 1,000 rpm and the reacted while supplying ethylene gas under pressure of 10 kg/cm$^2$G for 3 hours. The results are shown in Table 5.

TABLE 5

| Example No. | Solid Base Kind | grams | Conversion of Cumene (%) | Selectivity of TAB (%) |
|---|---|---|---|---|
| 22 | N | 0.44 | 99.6 | 97.8 |
| 23 | O | 0.45 | 88.9 | 97.4 |
| Comp. 6 | Q | 1.50 | 24.0 | 61.4 |
| Comp. 7 | R | 1.62 | 30.6 | 65.0 |
| Comp. 8 | Mixture | 8.49 | 19.4 | 73.9 |

EXAMPLE 24

In a 300 ml autoclave equipped with a magnetic stirrer having a nitrogen interior atmosphere, Solid Base N (1.07 g) and cumene (80 g) were charged and then liquid propylene (100 ml) was injected under pressure. The reaction was carried out at 160° C. for 24 hours.

After the reaction, the catalyst was filtered off and the reaction product was analyzed with gas chromatography. The results are shown in Table 6.

The catalyst was still active at the end of the reaction and the alkylation could be further carried out by using the same catalyst.

COMPARATIVE EXAMPLE 9

In the same manner as in Example 24 but using Solid Base S in place of Solid Base N, the alkylation was carried out. The results are shown in Table 6.

TABLE 6

| Example No. | Solid Base Kind | grams | Propylene (ml) | Time (hrs) | Conversion of Cumene (%) | Selectivity of TMPB (%) |
|---|---|---|---|---|---|---|
| 24 | N | 1.07 | 100 | 24 | 69.2 | 86.6 |
| Comp. 9 | S | 1.16 | 60 | 20 | 5.0 | 86.0 |

EXAMPLE 25

In a 300 ml autoclave equipped with a magnetic stirrer having a nitrogen interior atmosphere, Solid Base N (3.6 g) and toluene (79.5 g) were charged and then liquid propylene (70 ml) was injected under pressure.

The mixture was thereafter stirred at 163° C. for 6 hours.

After the reaction, the product was analyzed with gas chromatography. The results are shown in Table 7.

EXAMPLE 26 AND COMPARATIVE EXAMPLES 10-11

In the same manner as in Example 25 but using one of Solid Bases O, P and S in place of Solid Base N, the alkylation was carried out. The results are shown in Table 7.

In Examples 25 and 26, the catalyst was still active at the end of the reaction and the alkylation could be further carried out by using the same catalyst.

TABLE 7

| Example No. | Solid Base Kind | grams | Conversion of Toluene (%) | Selectivity of IBB (%) |
|---|---|---|---|---|
| 25 | N | 3.60 | 33.2 | 92.0 |
| 26 | O | 3.33 | 32.1 | 91.9 |
| Comp. 10 | P | 3.39 | 11.0 | 92.3 |
| Comp. 11 | S | 2.64 | 9.4 | 86.1 |

EXAMPLE 27

In a 300 ml autoclave equipped with a magnetic stirrer, Solid Base A (0.44 g) and p-diisoprpylbenzene (hereinafter referred to as "DIPB") (78.7 g) were charged under nitrogen, heated to 70° C. while stirring at 1,000 rpm and reacted at the same temperature for 3 hours while supplying ethylene gas under pressure of 5 kg/cm$^2$G.

After the reaction, the autoclave was cooled and the catalyst was filtered off. The reaction product was analyzed by gas chromatography to find that it contained DIPB (0.1%), p-isopropyl-tert.-amylbenzene (17.8%) and p-di-tert.-butylbenzene (79.7%).

Preparation of Solid Base T

In the same manner as in the preparation of Solid Base A but adding potassium hydroxide at 390° C., sintering the mixture of the alumina and potassium hydroxide at 390° C. and using metal sodium (1.25 g) in place of metal potassium, Solid Base T was prepared.

EXAMPLE 28

In the same manner as in Example 1 but using Solid Base T (0.37 g) and cumene (80 g) and carrying out the reaction at 160° C. in a 200 ml autoclave, the alkylation was carried out. The conversion of cumene was 46.4%, and the selectivity of TAB was 98.6%.

In Example 28, the catalyst was still active at the end of the reaction and the alkylation could be further carried out by using the same catalyst.

What is claimed is:

1. A process for preparing an alkyl-substituted hydrocarbon comprising:
   alkylating an aromatic hydrocarbon having at least one hydrogen atom at an alpha-position in a side chain with an olefin in the presence of a solid base which is obtained by reacting alumina, an alkali metal hydroxide and an alkali metal as follows,
   (a) reacting the alumina with the alkali metal hydroxide under the following conditions,
      (1) at a temperature not lower than 200° C. and lower than 400° C. when said alkali metal hydroxide is potassium hydroxide and said alkali metal is sodium, or
      (2) at a temperature of 200° C. to 600° C. when said alkali metal hydroxide is potassium hydroxide and said alkali metal is other than sodium, or when the alkali metal hydroxide is other than potassium hydroxide; and then
   (b) reacting the product of step (a) with the alkali metal at a temperature of 200° C. to 600° C. in an inert gas atmosphere to obtain said solid base.

2. The process according to claim 1, wherein the alkali metal hydroxide is reacted at a temperature of 250° to lower than 400° C. when said alkali metal hydroxide is potassium hydroxide and said metal is sodium, or a temperature of 250° to 550° C. when said alkali metal hydroxide is potassium hydroxide and said alkali metal is other than sodium, or when the alkali metal hydroxide is other than potassium hydroxide.

3. The process according to claim 2, wherein the alkali metal hydroxide is reacted at a temperature of 250° to lower than 400° C. when said alkali metal hydroxide is potassium hydroxide and said metal is sodium or a temperature of 260° to 480°0 C. when said alkali metal hydroxide is potassium hydroxide and said alkali metal is other than sodium, or when the alkali metal hydroxide is other than potassium hydroxide.

4. The process according to claim 1, wherein the alkali metal hydroxide is at least one selected from the group consisting of sodium hydroxide and potassium hydroxide.

5. The process according to claim 1, wherein the amount of the alkali metal hydroxide is 5 to 40% by weight based on the weight of the alumina.

6. The process according to claim 1, wherein the alkali metal is reacted at a temperature of 200° to 450° C.

7. The process according to claim 1, wherein the alkali metal is at least one selected from the group consisting of sodium and potassium.

8. The process according to claim 1, wherein the alkali metal is potassium and the alumina and the alkali metal hydroxide are reacted at a temperature of 200° to 600° C. under conditions (2).

9. The process according to claim 1, wherein the alkali metal is sodium, the alkali metal hydroxide is potassium hydroxide, and the alumina and potassium hydroxide are reacted at a temperature of 200° to 390° C.

10. The process according to claim 1, wherein the alkali metal is sodium, the alkali metal hydroxide is sodium hydroxide, and the alumina and potassium hydroxide are reacted at a temperature of 200° to 600° C.

11. The process according to claim 1, wherein the amount of the alkali metal is 2 to 15% by weight based on the weight of the alumina.

12. The process according to claim 1, wherein the aromatic hydrocarbon having one hydrogen atom at the alpha-position in the side chain has 1 to 10 carbon atoms in the side chain.

13. The process according to claim 1, wherein the olefin has 2 to 20 carbon atoms.

14. The process according to claim 1, wherein the olefin is selected from the group consisting of ethylene and propylene.

15. The process according to claim 1, wherein the alkylation temperature is from 20° to 200° C.

* * * * *

UNITED STATES PATENT AND TRADEMARK OFFICE
CERTIFICATE OF CORRECTION

PATENT NO. : 5,347,062
DATED : September 13, 1994
INVENTOR(S) : Masami FUKAO, et al It is certified that error appears in the above-indentified patent and that said Letters Patent is hereby corrected as shown below:

Title page,
Changing the information in the section entitled "[30] Foreign Application Priority Data" such that the incorrect number for the third-listed Japanese Priority Document of "63-282933" is corrected so as to read --63-282993--.

Signed and Sealed this

Seventh Day of March, 1995

Attest:

BRUCE LEHMAN

Attesting Officer

Commissioner of Patents and Trademarks